(12) United States Patent
LaBelle et al.

(10) Patent No.: US 11,291,563 B2
(45) Date of Patent: Apr. 5, 2022

(54) PASSAGE-DEFINING PROSTHETIC LIMB STRUCTURE AND FABRICATION METHOD

(71) Applicant: Arizona Board of Regents on behalf of Arizona State University, Scottsdale, AZ (US)

(72) Inventors: Jeffrey LaBelle, Tempe, AZ (US); Courtney Mason, Chandler, AZ (US)

(73) Assignee: Arizona Board of Regents on Behalf of Arizona, Scottsdale, AZ (US)

( * ) Notice: Subject to any disclaimer, the term of this patent is extended or adjusted under 35 U.S.C. 154(b) by 202 days.

(21) Appl. No.: 16/806,418

(22) Filed: Mar. 2, 2020

(65) Prior Publication Data

US 2020/0276030 A1    Sep. 3, 2020

Related U.S. Application Data

(60) Provisional application No. 62/812,493, filed on Mar. 1, 2019.

(51) Int. Cl.
| | | |
|---|---|---|
| *A61F 2/60* | (2006.01) | |
| *A61F 2/76* | (2006.01) | |
| *A61F 2/50* | (2006.01) | |
| *A61F 2/80* | (2006.01) | |
| *A61F 2/70* | (2006.01) | |

(52) U.S. Cl.
CPC .............. *A61F 2/60* (2013.01); *A61F 2/5046* (2013.01); *A61F 2/76* (2013.01); *A61F 2/80* (2013.01); *A61F 2002/5001* (2013.01); *A61F 2002/5003* (2013.01); *A61F 2002/5006* (2013.01); *A61F 2002/5049* (2013.01); *A61F 2002/607* (2013.01); *A61F 2002/608* (2013.01); *A61F 2002/701* (2013.01); *A61F 2002/7605* (2013.01)

(58) Field of Classification Search
CPC ................ A61F 2/601; A61F 2002/607; A61F 2002/608
USPC .......................................................... 623/27
See application file for complete search history.

(56) References Cited

U.S. PATENT DOCUMENTS

| | | |
|---|---|---|
| 4,055,690 A | 10/1977 | Patterson |
| 7,797,072 B2 | 9/2010 | Summit |
| 8,613,716 B2 | 12/2013 | Summit et al. |
| 10,219,918 B2 | 3/2019 | LaBelle et al. |

(Continued)

OTHER PUBLICATIONS

U.S. Appl. No. 17/175,948, filed Feb. 15, 2021, LaBelle et al.

(Continued)

*Primary Examiner* — David H Willse
(74) *Attorney, Agent, or Firm* — Withrow & Terranova, P.L.L.C.; Vincent K. Gustafson

(57) ABSTRACT

A prosthetic device includes an internal frame assembled from multiple longitudinal members and multiple transverse members that are substantially planar in character and are arranged to be joined together. A medially arranged opening is defined in each transverse member, and is substantially registered with openings of adjacent transverse members to form a longitudinal passage, such as may be useful to receive an actuator and/or other items. At least some transverse members differ from one another in one or more of shape, length, or width. A covering member may be provided over the internal frame. Rear-facing gaps in transverse members may receive one or more elements such as dampers, batteries, or the like.

23 Claims, 14 Drawing Sheets

(56) References Cited

U.S. PATENT DOCUMENTS

| | | | |
|---|---|---|---|
| 10,323,008 | B2 | 6/2019 | LaBelle et al. |
| 10,925,755 | B2 | 2/2021 | Lathers et al. |
| 10,967,154 | B2 | 4/2021 | LaBelle et al. |
| 2017/0065439 | A1* | 3/2017 | LaBelle ............ A61F 2/60 |
| 2018/0161179 | A1* | 6/2018 | Sevier ............ A61F 2/60 |
| 2019/0160206 | A1 | 5/2019 | Lathers et al. |
| 2019/0328315 | A1 | 10/2019 | LaBelle et al. |
| 2019/0330163 | A1 | 10/2019 | LaBelle et al. |
| 2020/0170811 | A1 | 6/2020 | Smith et al. |

OTHER PUBLICATIONS

Author Unknown, "Flexure Test," Instron, available at least as early as Mar. 24, 2016, 3 pages, http://www.instron.us/en-us/our-company/library/test-types/flexure-test.

Biddiss, Elaine A. et al., "Upper limb prosthesis use and abandonment: A survey of the last 25 years," Prosthetics and Orthotics International, vol. 31, No. 3, Sep. 2007, pp. 236-257.

Carey, Stephanie L. et al., "Golf hand prosthesis performance of transradial amputees," Prosthetics and Orthotics International, vol. 39, No. 3, Feb. 2014, 4 pages.

Chiu, James et al., "Prediction of upper extremity impact forces during falls on the outstretched hand," Journal of Biomechanics, vol. 31, No. 12, Dec. 1998, pp. 1169-1176.

Cignoni, Paolo et al., "Field Aligned Mesh Joinery," ACM Transactions on Graphics, vol. 28, No. 4, Article 106, Aug. 2009, 13 pages.

Cignoni, Paolo et al., "Mesh Joinery: A Method for Building Fabricable Structures," European Research and Innovation, ERCIM News, vol. 101, 2015, pp. 44-45.

Davidson, Judith, "A Survey of the Satisfaction of Upper Limb Amputees with Their Prostheses, Their Lifestyles, and Their Abilities," Journal of Hand Therapy, vol. 15, No. 1, Mar. 31, 2002, pp. 62-70.

Gretsch, Kendall F. et al., "Development of novel 3D-printed robotic prosthetic for transradial amputees," Prosthetics and Orthotics International, vol. 40, No. 3, Jun. 1, 2016, Published Online May 1, 2015, 4 pages.

Herbert, Nicholas et al., "A preliminary investigation into the development of 3-D printing of prosthetic sockets," Journal of Rehabilitation Research and Development, vol. 42, No. 2, Mar./Apr. 2005, pp. 141-146.

LaBelle, Jeffrey, "Fishbone Prosthetic," Abstract, Arizona State University, Apr. 23, 2015, 2 pages.

McGimpsey, Grant et al., "Limb Prosthetics Services and Devices," Bioengineering Institute Center for Neuroprosthetics Worcester Polytechnic Institution, White Paper, 2008, 35 pages.

O'Connell, Colleen, "Upper Limb Prosthetic Services Post Haiti Earthquake: Experiences and Recommendations of Haiti-Based Rehabilitation Program," JPO Journal of Prosthetics and Orthotics, vol. 24, No. 2, Apr. 2012, pp. 77-79.

O'Keeffe, Bernard, "Prosthetic rehabilitation of the upper limb amputee," Indian Journal of Plastic Surgery, vol. 44, No. 2, May/Aug. 2011, pp. 246-252.

O'Neill, Ciaran, "An Advanced, Low Cost Prosthetic Arm," Proceedings of the IEEE Sensors, Nov. 2014, IEEE, pp. 494-498.

O'Sullivan, L.W. et al., "Forearm torque strengths and discomfort profiles in pronation and supination," Ergonomics, vol. 48, No. 6, May 15, 2005, pp. 703-721.

Oh, I. et al., "Proximal strain distribution in the loaded femur. An in vitro comparison of the distributions in the intact femur and after insertion of different hip-replacement femoral components," Abstract, Journal of Bone & Joint Surgery, American Volume, Jan. 1978, 2 pages.

Park, J., "GORA: Prosthetic leg for below knee amputee swimmer," Jisue Park Portfolio, retrieved on Aug. 7, 2018 from the internet <URL:https://www.jisuepark.com/gora>, 9 pages.

Russell, D. et al., "A Bench-Top Prototype of a Variable Stiffness Prosthesis," MEC '05 Intergrating Prosthetics and Medicine, 2005, UNB, 4 pages.

Schultz, Aimee E. et al., "Expert opinions on success factors for upper-limb prostheses," Journal of Rehabilitation Research and Development, vol. 44, No. 4, 2007, pp. 483-490.

Summit, "Cooper Hewitt Leg," Summit Industrial Design, retrieved Aug. 7, 2018 from the internet <URL:http://www.summtid.com/#/cooper-hewitt-leg/>, 6 pages.

Wijk, Ulrika et al., "Forearm amputees' views of prosthesis use and sensory feedback," Journal of Hand Therapy, vol. 28, No. 3, Jul.-Sep. 2015, pp. 269-278.

Ziegler-Graham, Kathryn et al., "Estimating the prevalence of limb loss in the United States: 2005 to 2050," Archives of Physical Medicine and Rehabilitation, vol. 89, No. 3, Mar. 31, 2008, pp. 422-429.

* cited by examiner

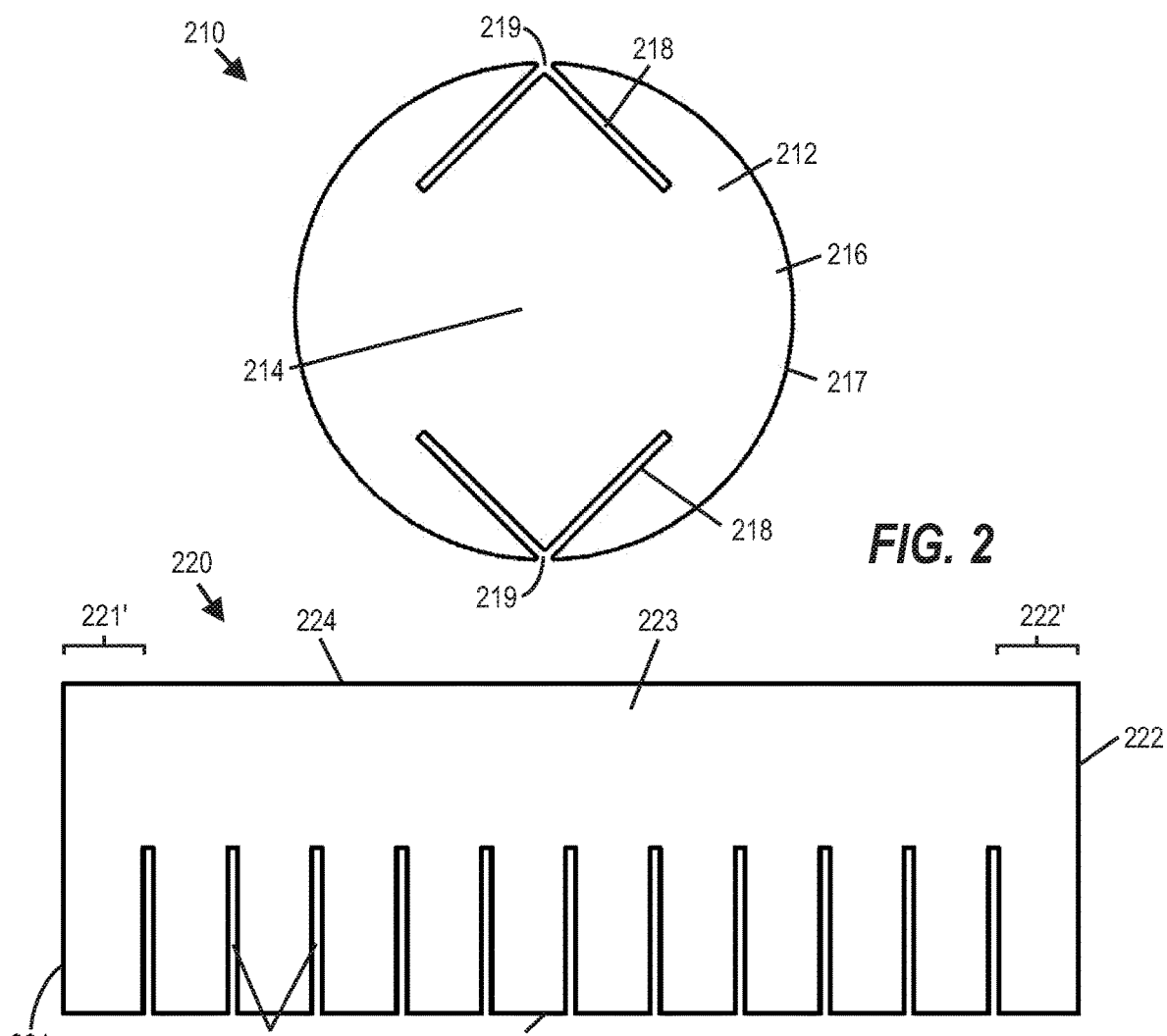
*FIG. 2*
*FIG. 3*
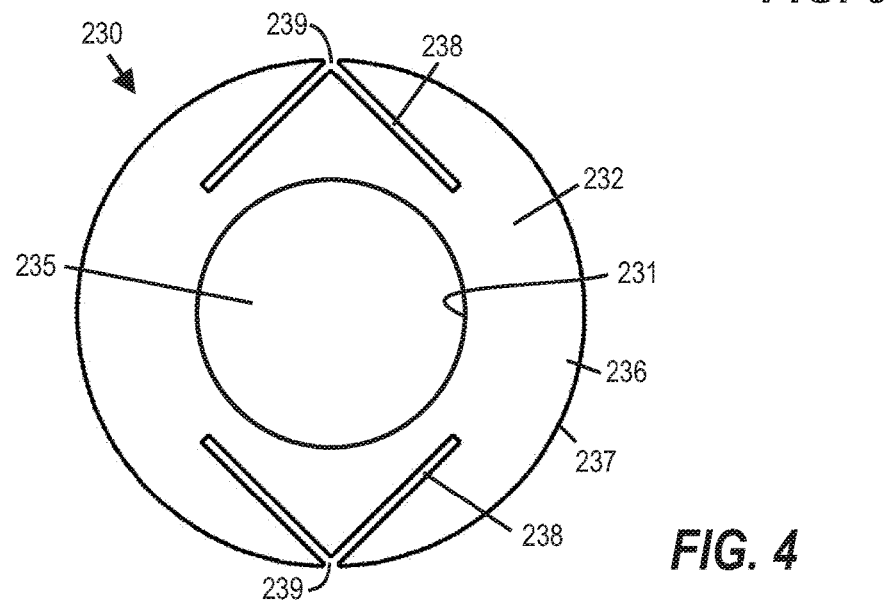
*FIG. 4*

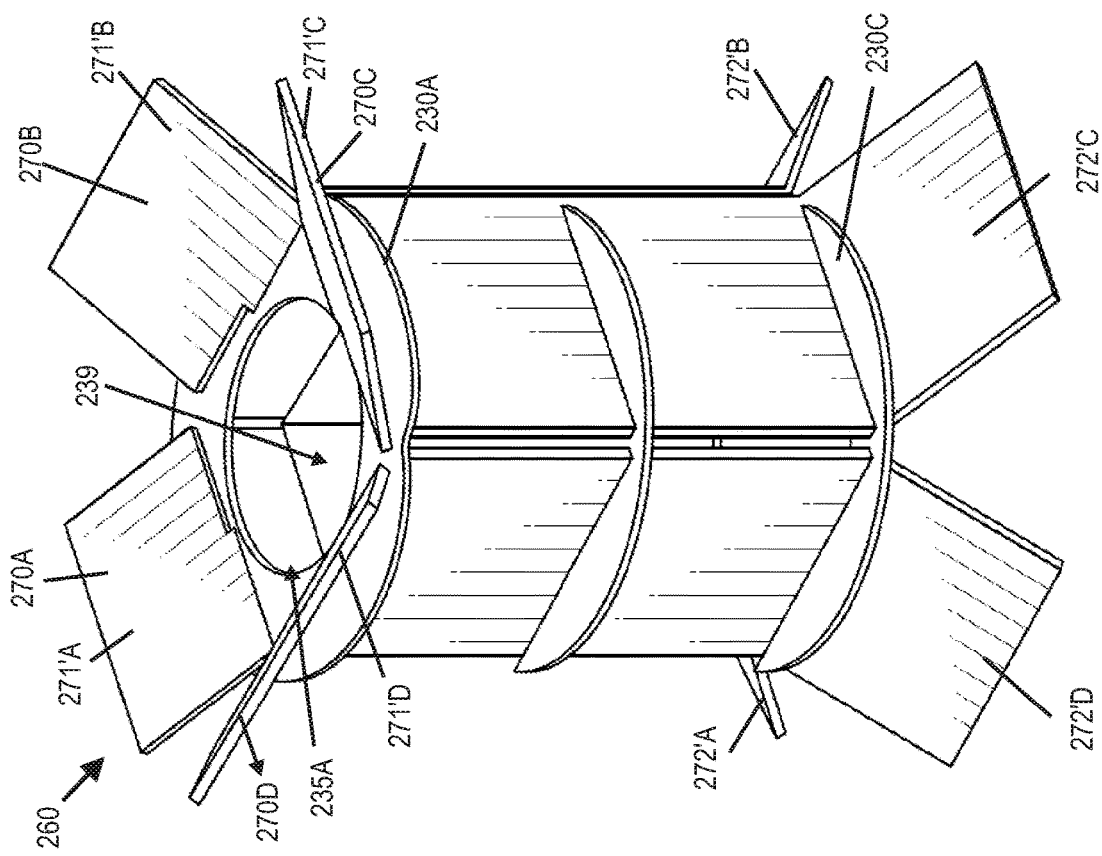
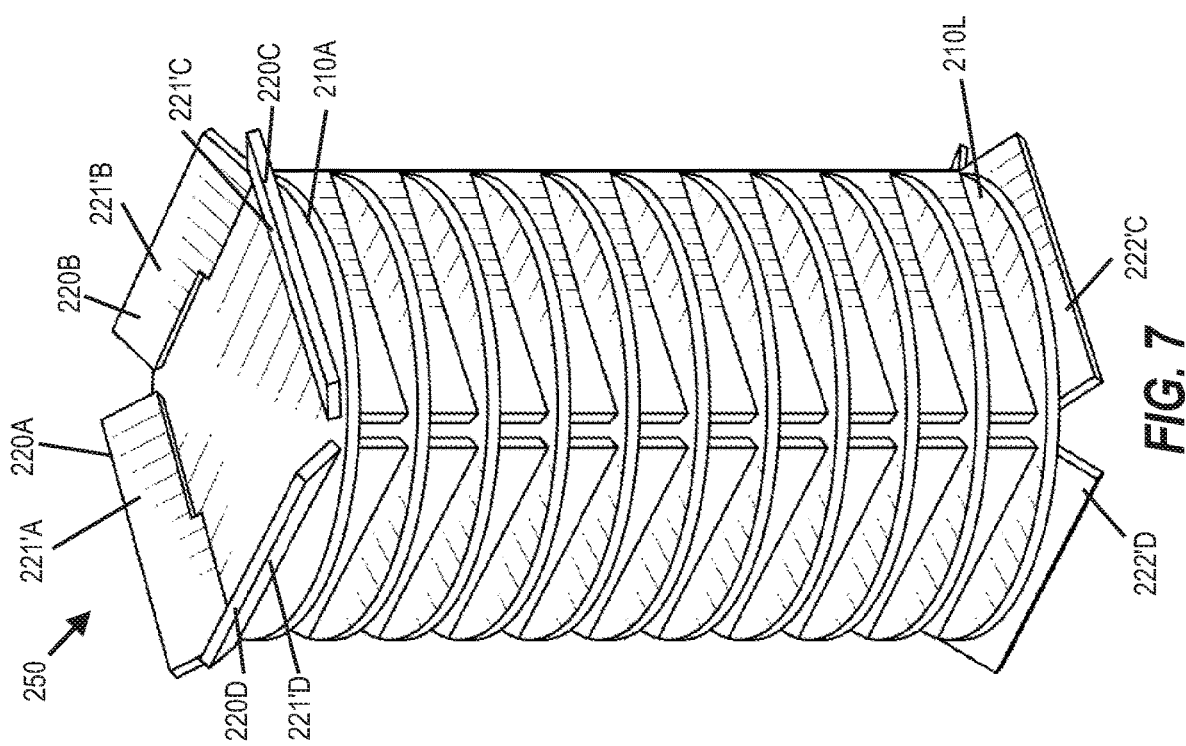

|  | Average Weight (g) | Interstitial Volume (cm$^3$) |
|---|---|---|
| 4 fin- no hole | 23.91 | 303.18 |
| 4 fin- 1.9 cm radius hole | 21.56 | 306.94 |
| 12 fin- no hole | 42.36 | 276.64 |
| 12 fin- 1.9 cm radius hole | 32.15 | 290.44 |

*FIG. 13*

|  | 4 fin- no hole | 4 fin- 1.9 cm radius hole | 12 fin- no hole |
|---|---|---|---|
| % Difference Weight | | | |
| 4 fin- 1.9 cm radius hole | 10.37% | | |
| 12 fin- no hole | 55.67% | 65.10% | |
| 12 fin- 1.9 cm radius hole | 29.37% | 39.44% | 27.42% |
| % Difference Interstitial Volume | | | |
| 4 fin- 1.9 cm radius hole | 1.23% | | |
| 12 fin- no hole | 9.15% | 10.38% | |
| 12 fin- 1.9 cm radius hole | 4.29% | 5.52% | 4.87% |

*FIG. 14*

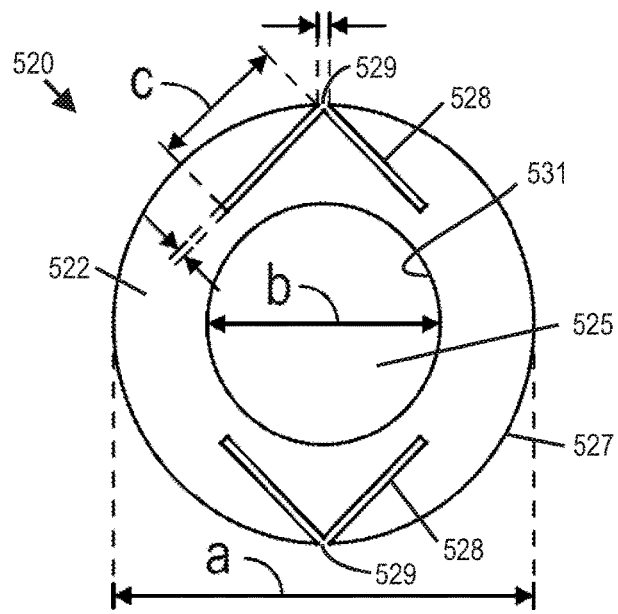
*FIG._19*
| | Fin 0 | Fin 14 |
|---|---|---|
| a | 6.18 | 8 |
| b | 3.4 | 4.42 |
| c | 2 | 2.6 |
| d | 4.15 | 5.395 |
| e | 2.1 | 2.61 |
| f | 1.39 | 1.807 |
| g | 4.37 | 0 |
*FIG._21*
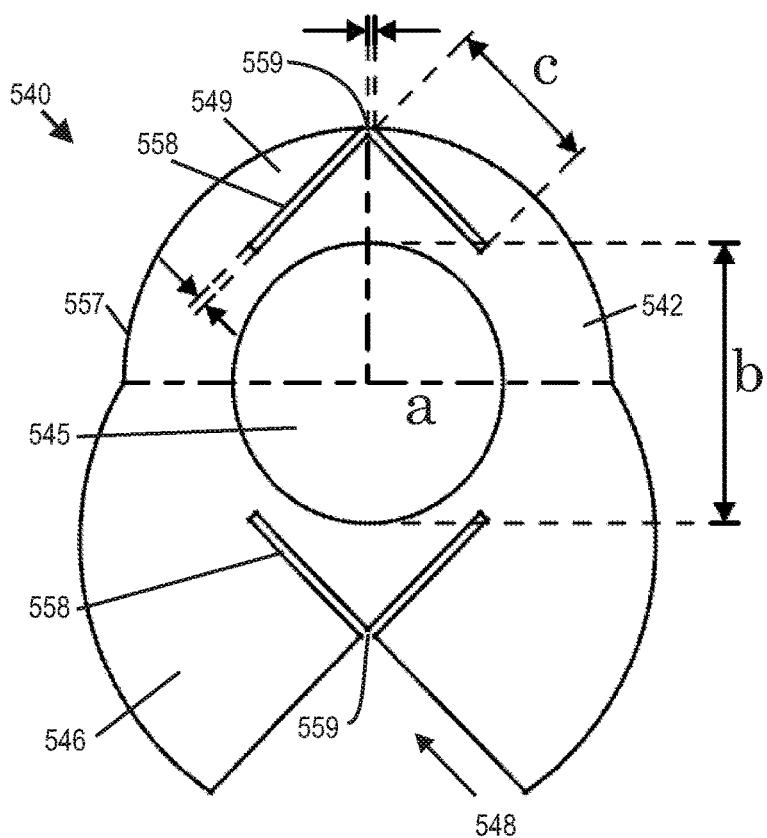
*FIG._20*

US 11,291,563 B2

PASSAGE-DEFINING PROSTHETIC LIMB STRUCTURE AND FABRICATION METHOD

CROSS-REFERENCE TO RELATED APPLICATION(S)

This application claims priority to U.S. Provisional Patent Application No. 62/812,493 filed on Mar. 1, 2019, wherein the entire disclosure of the foregoing application is hereby incorporated by reference herein.

TECHNICAL FIELD

This disclosure relates to prosthetic devices, including artificial limbs and portions thereof, and methods for fabricating such devices.

BACKGROUND

In the United States, about two million people have lost a limb, with hospital costs for amputations of approximately $8.3 billion each year. It is estimated that the total number of lower limb amputees in the United States is about 1.46 million, with the number of transtibial or below-the-knee amputees growing by about 185,000 per year. 54% of limb losses are attributable to vascular diseases, including diabetes and peripheral arterial disease; about 45% of limb losses are attributable to physical trauma; and fewer than 2% of limb losses are attributable to cancer, with a ratio of upper limb to lower limb loss of 1:4. Prosthetics can cost up to $50,000 per limb, and a significant number (possibly a majority) are not covered by insurance. Additionally, many prosthetics need to be replaced as the user grows, and health insurance frequently does not cover the cost of continual replacement.

Current state of the art designs for below the knee (BTK) prosthetics features a simple titanium post for the load bearing portion of the prosthetic. FIG. 1 shows a conventional prosthetic leg 101 having a socket 121 with a recessed surface arranged to engage an end of a user's amputated limb (e.g., remaining leg portion). The socket 121 may embody a padded plastic structure that distributes compressive forces on the end of the amputated limb. The bottom of the socket 121 is attached to a pylon 123 which may embody a tubular metal (e.g., titanium) support. The bottom of the pylon 123 may attach to an artificial foot 125 that can be a molded plastic structure. The prosthetic leg 101 may include a foam covering 127 that can be attached to the socket 121 and the pylon 123 to provide a more lifelike shape. Components of the prosthetic leg 101 can be coupled together using fasteners such as screws, bolts, and adhesives.

Current BTK prosthetic designs can be uncomfortable for patients. Typically, patients most frequently report that discomfort emanates from the socket. However, there is a source of discomfort that patients might not link to their prosthetic or simply attribute it to prosthetic use. Titanium pylons may be too strong and rigid for gait impact while using the prosthetic. Although light and easily manufactured, a typical pylon doesn't yield at all on impact and can send shock forces up the stump, through the thigh, and can affect the hip and back. Typically, such forces are softened by the ankle pad and lower limb joints, but amputees lack such cushioning, and the knee joint not only is under new stresses from the socket but also takes more shock due to the lack of padding. Additionally, BTK prosthetics users have asymmetrical and compensatory gaits due to the loss of the ankle plantar flexors, which can further aggravate the effects of the pylon. While this is a concern for amputee athletes, it can also cause problems with overweight amputees (which make up a significant portion of BTK amputees due to Type II Diabetes). Any patient with a BTK amputation therefore could experience these issues.

Currently, shock absorbing pylons include spring-like mechanisms so the pylon shortens with axial loads. At best, the effectiveness of shock absorbing pylons is inconsistent; at worst, they have no effect. This may be attributable in part to the fact that during heel strike, the load is not axial, since the leg is at a non-vertical angle when ground contact is made.

Functional prosthetics include categories of body-powered and externally-powered prosthetics. Body-powered prosthetics typically use cables and harnesses strapped to the individual to mechanically maneuver the artificial limb, but can be fatiguing to operate. Externally powered artificial limbs, including myoelectric prosthetics, seek to reduce user fatigue using batteries and electronic systems to control movement. A myoelectric prosthetic may be attached to a user's remaining limb portion using suction technology or other means, and sensors may be used to detect minute muscle, nerve, and electromyographic activity. Muscle activity triggered by a user is translated into information used by electric motors to control movement of the artificial limb. Myoelectric limbs may look and even move much like a natural limb. The primary disadvantages to such limbs are weight and cost. Moreover, endoskeletal designs leave limited room for other prosthetic components.

Prosthetics with endoskeletal structures or exoskeletal structures are known. Endoskeletal prosthetics include at least one internal support, such as an aluminum, titanium, or carbon fiber pylon. Exoskeletal prosthetics include an outer structure providing structural rigidity, typically including laminated reinforcement materials such as fiberglass, nylon, Dacron®, carbon fiber, and Kevlar®, which may be bound with polymer resin. Depending on the skeletal structure, providing sufficient space and convenient passage for actuating components can present challenges. It can also be challenging to tailor the size, shape, and appearance of a prosthetic to match a remaining limb of a user in a rapid and cost-effective manner.

Due to their custom character and potentially high complexity, prosthetic devices typically require significant manufacturing time and entail high production costs. Need exists for prosthetic devices and prosthetic device fabrication methods to address limitations of conventional devices and methods.

BRIEF DESCRIPTION OF DRAWINGS

FIG. 2 is a top plan view of a substantially planar transverse member of an internal frame of a comparison prosthetic device, with the transverse member including a generally round body and four peripheral slots arranged in two groups of two slots.

FIG. 3 is a top plan view of a substantially planar longitudinal member useable with the transverse member of FIG. 2 to form an internal frame of a comparison prosthetic device, with the longitudinal member having a rectangular shape with eleven peripheral slots arranged along one elongated straight edge.

FIG. 4 is a top plan view of a substantially planar transverse member of an internal frame of prosthetic device according to one embodiment, with the transverse member including a generally round body defining a medial opening and defining four peripheral slots arranged in two groups of two slots.

FIG. 7 illustrates the internal frame of a comparison prosthetic device according to the design of FIG. 5 following performance of compression testing, showing deformation of end portions of the longitudinal members extending beyond the uppermost and lowermost transverse members.

FIG. 8 illustrates the internal frame of a prosthetic device according to the design of FIG. 6 (i.e., according to one embodiment of the present disclosure) following performance of compression testing, showing deformation of end portions of the longitudinal members extending beyond the uppermost and lowermost transverse members.

FIG. 13 is a table identifying average weight and interstitial volume values for internal frames of prosthetic devices according to four different designs.

FIG. 14 is a table identifying percentage differences in weight and in interstitial volume for the latter three internal frame designs of FIG. 13 in comparison to one another and in comparison to the first internal frame design of FIG. 13.

FIG. 19 is a top plan view illustration of a substantially planar transverse member arranged to form a lower portion of an internal frame of prosthetic device according to one embodiment.

FIG. 20 is a top plan view illustration of a substantially planar transverse member arranged to form an upper lower portion of an internal frame of prosthetic device according to one embodiment.

FIG. 21 is a table identifying six dimensional values for each of two transverse members (or fins) of a prosthetic device incorporating the transverse members of FIGS. 19 and 20.

DETAILED DESCRIPTION

Figure 1:
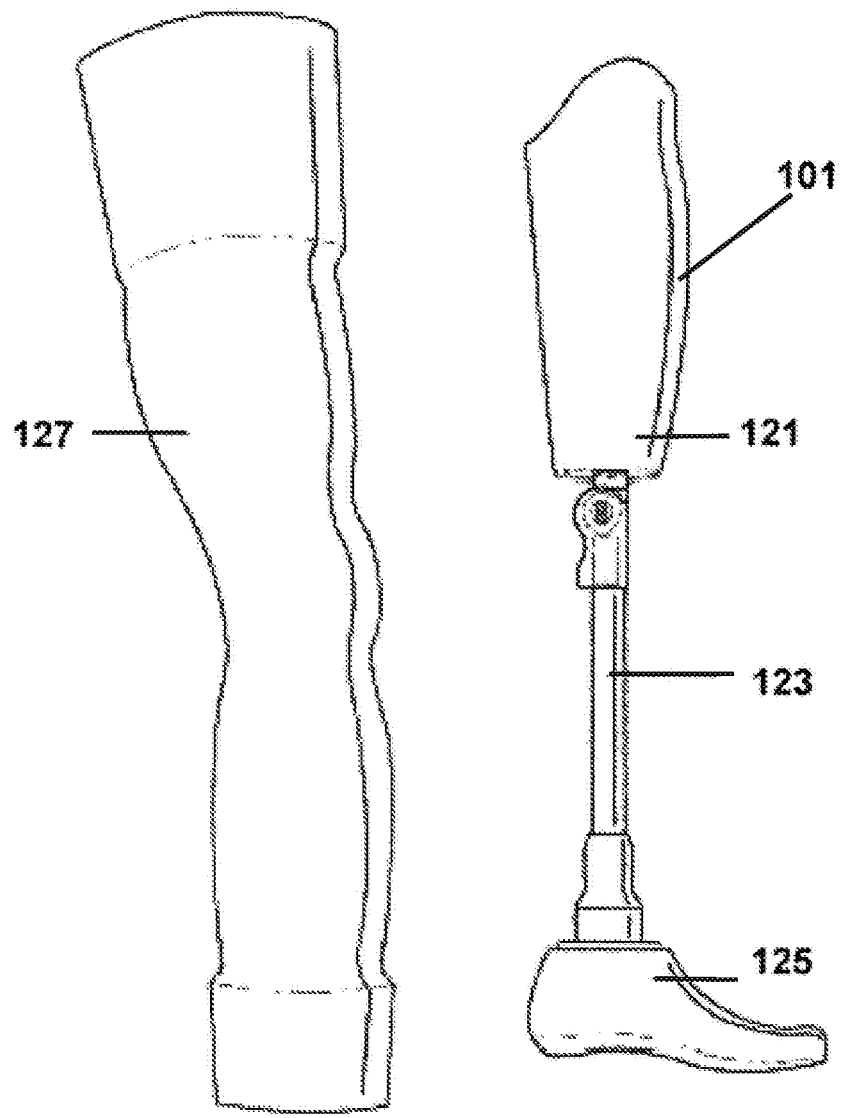
FIG. 1 is an elevation view of components of a conventional prosthetic leg.

In certain aspects, a prosthetic device includes an internal frame assembled from multiple longitudinal members and multiple transverse members, wherein each member is substantially planar and defines peripheral slots therethrough, and wherein the longitudinal members and transverse members are arranged to mate with one another to join the longitudinal members with the transverse members. Each transverse member defines a medially arranged opening, and the medially arranged opening of each transverse member is substantially registered with the medially arranged opening of at least one adjacent transverse member. At least some transverse members of the plurality of transverse members differ from other transverse members of the plurality of transverse members in one or more of shape, length, or width. Longitudinal and transverse members of various materials may be used to produce lightweight and crush-resistant prosthetic device structures capable of withstanding substantial axial and torsional loads.

Substantially planar longitudinal members and transverse members can be fabricated using various materials and various fabrication techniques. Examples of materials that may be used according to certain embodiments include, but are not limited to, the following: polymeric materials, fiber-reinforced materials, composites, laminated composites, multi-layer laminates, carbon fiber, paperboard, wood-based materials, fiberglass, metals, metallic materials, and combinations of two or more of the foregoing. Examples of techniques that may be used to produce longitudinal members and transverse members include, but are not limited to, the following: thermoforming, molding, stamping, forging, casting, milling, blade cutting, laser cutting, liquid jet cutting, three-dimensional printing, multi-layer additive material deposition, and combinations of two or more of the foregoing.

The term "substantially planar" as used herein refers to an element preferably having length and width dimensions that substantially exceed a thickness dimension, wherein at least one face is preferably substantially flat in character. In certain embodiments, length and/or width dimensions of substantially planar members disclosed herein each exceed corresponding thickness dimensions by a factor of at least five, at least ten, at least fifteen, at least twenty, at least thirty, at least forty, at least fifty, at least seventy-five, or at least one hundred.

In certain embodiments, at least some transverse members (or all transverse members) may be arranged along planes substantially parallel to one another.

In certain embodiments, at least some transverse members, at least two transverse members, or all transverse members, may be arranged substantially perpendicular to longitudinal members with which the transverse members are assembled.

In certain embodiments, the plurality of longitudinal members is devoid of any longitudinal members that are radially arranged relative to a central axis extending through the plurality of transverse members. In certain embodiments, the plurality of longitudinal members consists of four longitudinal members.

In certain embodiments, longitudinal members of the plurality of longitudinal members are tangentially arranged relative to an imaginary circle concentrically arranged with the central axis, wherein the imaginary circle comprises a diameter smaller than a lateral extent of each transverse member of the plurality of transverse members.

In certain embodiments, at least some transverse members of a plurality of transverse members may be bonded to a plurality of longitudinal members. Examples of bonding techniques that may be used include, but are not limited to, adhesive bonding, solvent bonding, thermal bonding, welding, and the combinations of the foregoing. In certain embodiments, two-part adhesives such as epoxies may be used. If employed, adhesives may be applied using techniques such as brushing, spraying, dipping, rolling, or other techniques.

In certain embodiments, one or more outer shaping members may be arranged to cover at least a portion of an internal frame as described herein. In certain embodiments, at least a portion of an outer shaping member may include a tubular shape. In certain embodiments, an outer shaping member may be bonded to outermost surfaces of a frame (e.g., edges of longitudinal and/or transverse members, and/or faces of transverse members). In certain embodiments, an outer shaping member may be removably applied over portions of a frame via methods such as rolling or sliding. In certain embodiments, an outer shaping member may be removably applied over portions of a frame without permanent bonding, such as to permit servicing or replacement of components (e.g., actuators, energy storage elements, sensors, control elements, etc.) that may be arranged in interstices or voids within the internal frame. In certain embodiments, an outer shaping member may be arranged to compress portions of the internal frame to enhance its rigidity and/or inhibit unintended separation between structural members. In certain embodiments, an outer shaping member may embody a substantially continuous material. In other embodiments, an outer shaping member may embody one or more holes or voids.

In certain embodiments, one or more dimensions of a prosthetic recipient may be measured, and longitudinal and/or transverse members may be fabricated responsive to such measurement, with such members being assembled thereafter to form an internal frame of the prosthetic device. In this manner, an internal frame of a prosthetic device may be custom-built for a specific recipient. If a prosthetic recipient has an intact limb, then the intact limb may be measured to permit an internal frame of a prosthetic device to match dimensions of the intact limb as closely as possible.

In certain embodiments, at least one of an actuator or a control element extends through medially arranged openings of multiple transverse members of the plurality of transverse members. Additionally, or alternatively, gaps or spaces between assembled members may be used for receiving functional elements such as actuators (e.g., motors, solenoids, pistons, etc.), energy storage elements (e.g., batteries), control elements, sensors, and the like.

In certain embodiments, two or more transverse members of the plurality of transverse members each define a peripheral recess, wherein for each transverse member of the two or more transverse members, at least two peripheral slots of the plurality of second peripheral slots extend from the peripheral recess into an interior of the transverse member without intersecting the medially arranged opening. In certain embodiments, the peripheral recess of each transverse member of the two or more transverse members is registered with the peripheral recess of each other transverse member of the two or more transverse members.

In certain embodiments, two or more transverse members of the plurality of transverse members each define a peripheral recess, wherein the peripheral recess of each transverse member of the two or more transverse members is registered with the peripheral recess of each other transverse member of the two or more transverse members.

In certain embodiments, a socket is positioned at an upper end of the internal frame, wherein the socket is configured to receive a residual limb of the human user.

In certain embodiments, a prosthetic device further comprises at least one of an actuator, an energy storage element, a sensor, or a control element arranged in the peripherally arranged recesses of the two or more transverse members. In certain embodiments, an outer shaping member is arranged to cover and compressively engage at least a portion of the internal frame.

In certain embodiments, longitudinal members may include symmetrical length and/or width dimensions. In other embodiments, one or more portions of longitudinal members and/or transverse members may be asymmetric in character. In certain embodiments, some transverse members are circular in shape, and other transverse members may be non-circular in shape.

In certain embodiments, multiple longitudinal members within a single frame may comprise substantially the same dimensions. In other embodiments, different longitudinal members within a single frame may comprise different dimensions relative to one another.

In certain embodiments, multiple transverse members within a single frame may comprise substantially the same dimensions, while other transverse members may comprise different dimensions. In other embodiments, all transverse members within a single frame may comprise different dimensions relative to one another.

In certain embodiments, longitudinal members within a single frame may comprise a substantially uniform thickness. In certain embodiments, different longitudinal members within a single frame may comprise different thicknesses. In certain embodiments, thickness of one or more longitudinal members may be subject to vary within each respective longitudinal member.

In certain embodiments, transverse members within a single frame may comprise a substantially uniform thickness. In certain embodiments, different transverse members within a single frame may comprise different thicknesses. In certain embodiments, thickness of one or more transverse members may be subject to vary within each respective transverse member.

In one embodiment, a prosthetic device includes an internal frame, wherein the internal frame includes a plurality of longitudinal members and a plurality of transverse members. Each longitudinal member is substantially planar and includes a plurality of first peripheral slots defined through an entire thickness of the respective longitudinal member.

Each transverse member is substantially planar and includes a plurality of second peripheral slots defined through an entire thickness of the respective transverse member. Each first peripheral slot of the plurality of first peripheral slots is arranged to mate with a different second peripheral slot of the plurality of second peripheral slots, to join the plurality of longitudinal members with the plurality of transverse members. Each transverse member defines a medially arranged opening, and the medially arranged opening of each transverse member is substantially registered with the medially arranged opening of at least one adjacent transverse member. At least some transverse members of the plurality of transverse members differ from other transverse members of the plurality of transverse members in one or more of shape, length, or width.

In one embodiment, a method for fabricating a prosthetic device utilizes a plurality of substantially planar longitudinal members and a plurality of substantially planar transverse members as disclosed herein. Each longitudinal member includes a plurality of first peripheral slots defined through an entire thickness of the longitudinal member, and each transverse member includes a plurality of second peripheral slots defined through an entire thickness of the transverse member. The method includes mating each first peripheral slot of the plurality of first peripheral slots with a different second peripheral slot of the plurality of second peripheral slots to join the plurality of longitudinal members with the plurality of transverse members to form an internal frame of the prosthetic device.

In certain embodiments, the method further comprises bonding at least some transverse members of the plurality of substantially planar transverse members to the plurality of substantially planar longitudinal members.

In certain embodiments, the method further comprises providing an outer shaping member to cover at least a portion of the internal frame.

In certain embodiments, the method further comprises measuring one or more dimensions of a prosthetic recipient, and fabricating (i) the plurality of substantially planar longitudinal members and/or (ii) the plurality of substantially planar transverse members responsive to said measuring.

In certain embodiments, the method further comprises fabricating at least some members of (i) the plurality of substantially planar longitudinal members and/or (ii) the plurality of substantially planar transverse members by at least one step selected from thermoforming, molding, stamping, or casting.

In certain embodiments, the method further comprises fabricating at least some members of (i) the plurality of substantially planar longitudinal members and/or (ii) the plurality of substantially planar transverse members by at least one step selected from milling, blade cutting, laser cutting, or liquid jet cutting.

In certain embodiments, the method further comprises fabricating at least some members of (i) the plurality of substantially planar longitudinal members and/or (ii) the plurality of substantially planar transverse members by at least one step selected from three-dimensional printing or multi-layer additive material deposition.

FIGS. 2 and 3 illustrate a transverse member 210 and a longitudinal member 220, respectively, that may be used to fabricate a comparison prosthetic device to provide a basis for comparing prosthetic devices according to embodiments of the present disclosure. It is noted that longitudinal member 220 of FIG. 3 may also be used with transverse members other than the transverse member 210 of FIG. 2 according to embodiments herein.

The transverse member 210 of FIG. 2 includes a generally round body 212 and four peripheral slots 218, arranged as two pairs of slots 218 each in a chevron configuration. The body 212 includes a central portion 214 arranged generally between the pairs of slots 218, and a peripheral portion 216 arranged outside of the central portion 214. Each pair of slots 218 has a single slot opening 219 arranged along an outer edge 217 of the body 212. The body 212 is devoid of any opening in the central portion 214.

FIG. 3 is a top plan view of a substantially planar longitudinal member 220 useable with a plurality of transverse members 210 according to FIG. 2 to form an internal frame of a comparison prosthetic device. The longitudinal member 220 has a rectangular shape with two ends 221, 222, opposing first and second lengthwise edges 224, 225, and eleven peripheral slots 226 arranged along the first lengthwise edge 225. The second lengthwise edge 224 is devoid of any peripheral slots. End portions 221', 222' are arranged between outermost peripheral slots 226 and the ends 221, 222 of the longitudinal member 220.

FIG. 4 is a top plan view of a substantially planar transverse member 230 of an internal frame of prosthetic device according to one embodiment, with the transverse member 230 including a generally round body 232 defining a medial opening 235 and defining four peripheral slots 238, arranged as two pairs of slots 238 each in a chevron configuration. The medial opening 235 is bounded by an inner edge 231 and is arranged between the pairs of slots 238, and a peripheral portion 236 of the body 232 is arranged generally outside of the slots 238. Each pair of slots 238 has a single slot opening 239 arranged along an outer edge 237 of the body 232.

Figure 5:
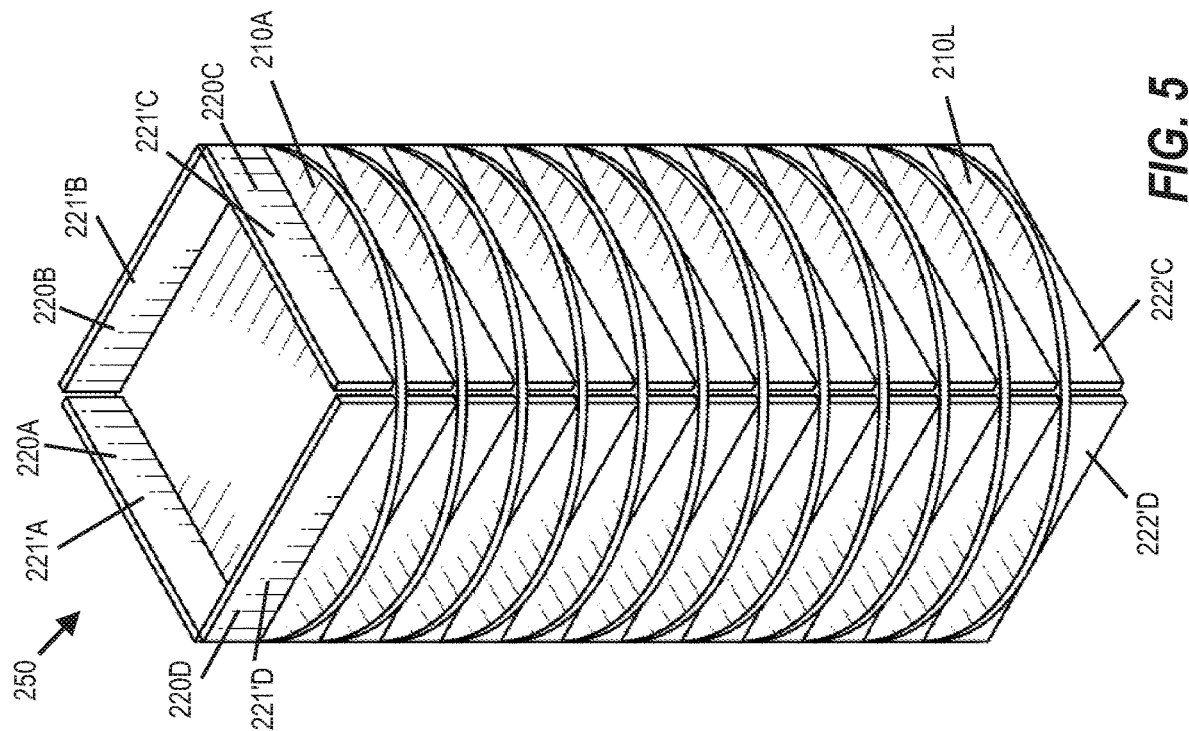
FIG. 5 is a perspective view of an internal frame of a comparison prosthetic device assembled from eleven transverse members according to FIG. 2 and four longitudinal members according to FIG. 3.

FIG. 5 is a perspective view of a an internal frame 250 of a comparison prosthetic device assembled from eleven transverse members 210A-210L according to FIG. 2 and four longitudinal members 220A-220D according to FIG. 3. As shown, the internal frame 250 has a generally cylindrical shape defined by edges of the transverse members 210A-210L, with end portions 221'A-221'D, 222'A-222'D of the longitudinal members 220A-220D in combination forming square shapes that extend above and below the uppermost and lowermost transverse members 210A, 210L, respectively.

Figure 6:
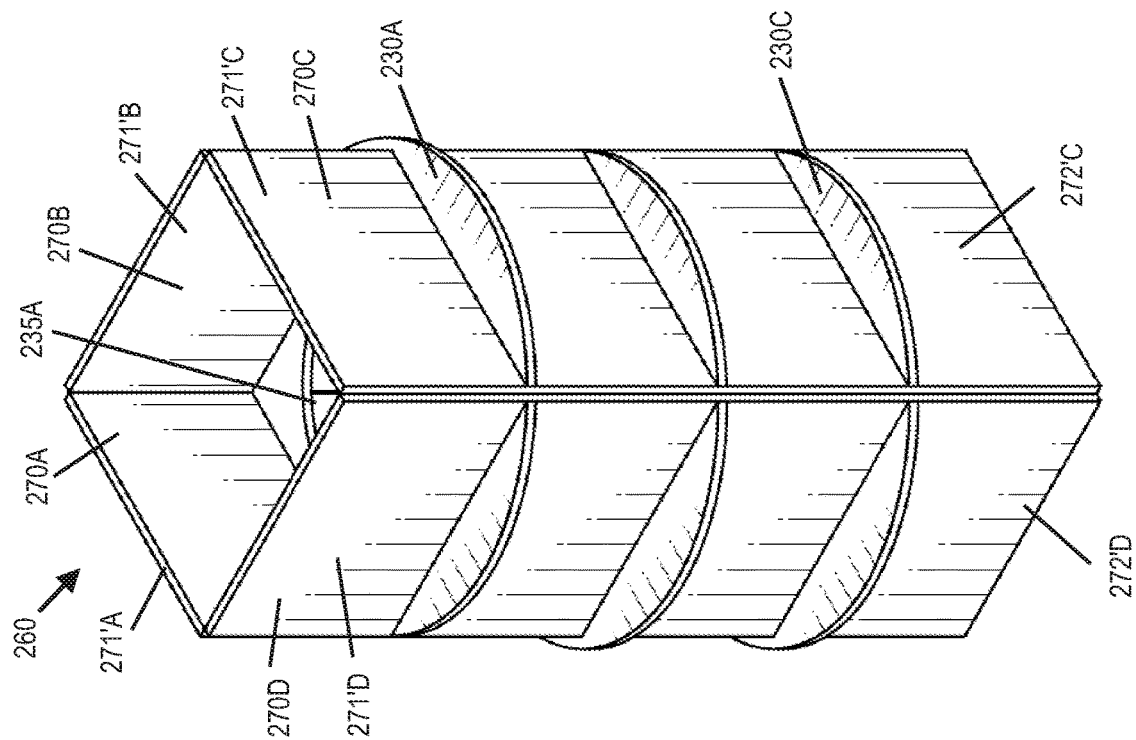
FIG. 6 is a perspective view of an internal frame of a prosthetic device according to one embodiment assembled from three transverse members according to FIG. 4 and four longitudinal members similar to those depicted in FIG. 3 but having fewer peripheral slots (i.e., three versus eleven peripheral slots).

FIG. 6 is a perspective view of an internal frame 260 of a prosthetic device according to one embodiment assembled from three transverse members 230A-230C according to FIG. 4 and four longitudinal members 270A-270D similar to those depicted in FIG. 3 but having fewer peripheral slots (i.e., three versus eleven peripheral slots). As shown, the internal frame 260 has a generally cylindrical shape defined by edges of the three transverse members 230A-230C, with end portions 271'A-271'D, 272'A-272'D of the longitudinal members 270A-270D in combination forming square shapes that extend above and below the uppermost and lowermost transverse members 230A-230C, respectively. A medial opening (e.g., 235A) extends through each transverse member 230A-230C.

FIG. 7 illustrates the internal frame 250 of a comparison prosthetic device according to the design of FIG. 5 following performance of compression testing, showing deformation of the end portions 221'A-221'D, 222'A-222'D of the longitudinal members 220A-220D extending beyond the uppermost and lowermost transverse members 210A-210L, respectively. According to one implementation used for compression testing, the longitudinal members 220A-220D and transverse members 210A-210L were fabricated of 0.062 inch (0.13 cm) thickness chipboard material, and the internal frame 250 had a diameter of 6.18 cm and a height of 12 cm. Although the end portions 221'A-221'D, 222'A-222'D of the longitudinal members 220A-220D extending beyond the uppermost and lowermost transverse members 210A, 210L were bent outward, the eleven transverse members 210A-210L remained spaced apart from one another without visible compression of the structure of the frame 250 between the transverse members 210A-210L.

FIG. 8 illustrates the internal frame 260 of a prosthetic device according to the design of FIG. 6 (i.e., according to one embodiment of the present disclosure) following performance of compression testing, showing deformation of end portions 271'A-271'D, 272'A-272'D of the longitudinal members 270A-270D extending beyond the uppermost and lowermost transverse members 230A, 230C. A medial opening (e.g., 235A) extends through each transverse member 230A-230C to form a longitudinal passage 239. According to one implementation used for compression testing, the longitudinal members 270A-270D and transverse members 230A-230C were fabricated of 0.062 inch (0.13 cm) thickness chipboard material, and the internal frame 260 had a diameter of 6.18 cm and a height of 12 cm. Although the end portions 271'A-271'D of the longitudinal members 270A-270D extending beyond the uppermost and lowermost transverse members 230A-230C were bent outward, the three transverse members 230A-230C remained spaced apart from one another without visible compression of the frame 260 between the transverse members 230A-230C.

Comparing FIGS. 7 and 8, the strength of the internal frames 250, 260 according to the two different designs appears to be relatively independent of the number of transverse members and relatively independent of the presence or absence of medial openings in the transverse members. In particular, ANOVA and T-testing revealed there was no significant difference in compression strength of any the designs, meaning the sparser designs with greater interstitial volume were just as compressively strong as the denser designs. Although the design of the internal frame 250 of FIG. 7 has a reasonable amount of interstitial space, the design of the internal frame 260 of FIG. 8 has significantly more interstitial space and provides an uninterrupted medial passage 239 through the frame. The sparser design of FIG. 8 was just as compressively strong at the denser design, but with significantly reduced total weight In one embodiment, the sparsest design weighted only 21.56 grams with an interstitial volume of 307 $cm^3$ (embodying values 65% lighter than the densest design, with 10% more interstitial volume), yet able to hold 608.4 N (about 137 pounds).

Various 12 cm tall cylindrical frame designs were laser cut (using a Universal Laser Systems laser cutter) and assembled. Designs with different numbers of transverse members (i.e., 11, 9, 7, 5, and 3 transverse fins, respectively), and with medial holes of differing radii (i.e., 0 cm, 1.1 cm, 1.3 cm, 1.5 cm, 1.7 cm, and 1.9 cm) were fabricated. Three samples of each transverse member and hole combination were fabricated. Samples were compressed in an Instron machine. For purposes of experimentation, mechanical failure was defined as the first deformation point, since any such deformation in a prosthetic leg would be catastrophic to the wearer. An algorithm was developed for converting cylindrical designs to a leg shape, and a sample full-size foreleg prototype was assembled.

Figure 9:
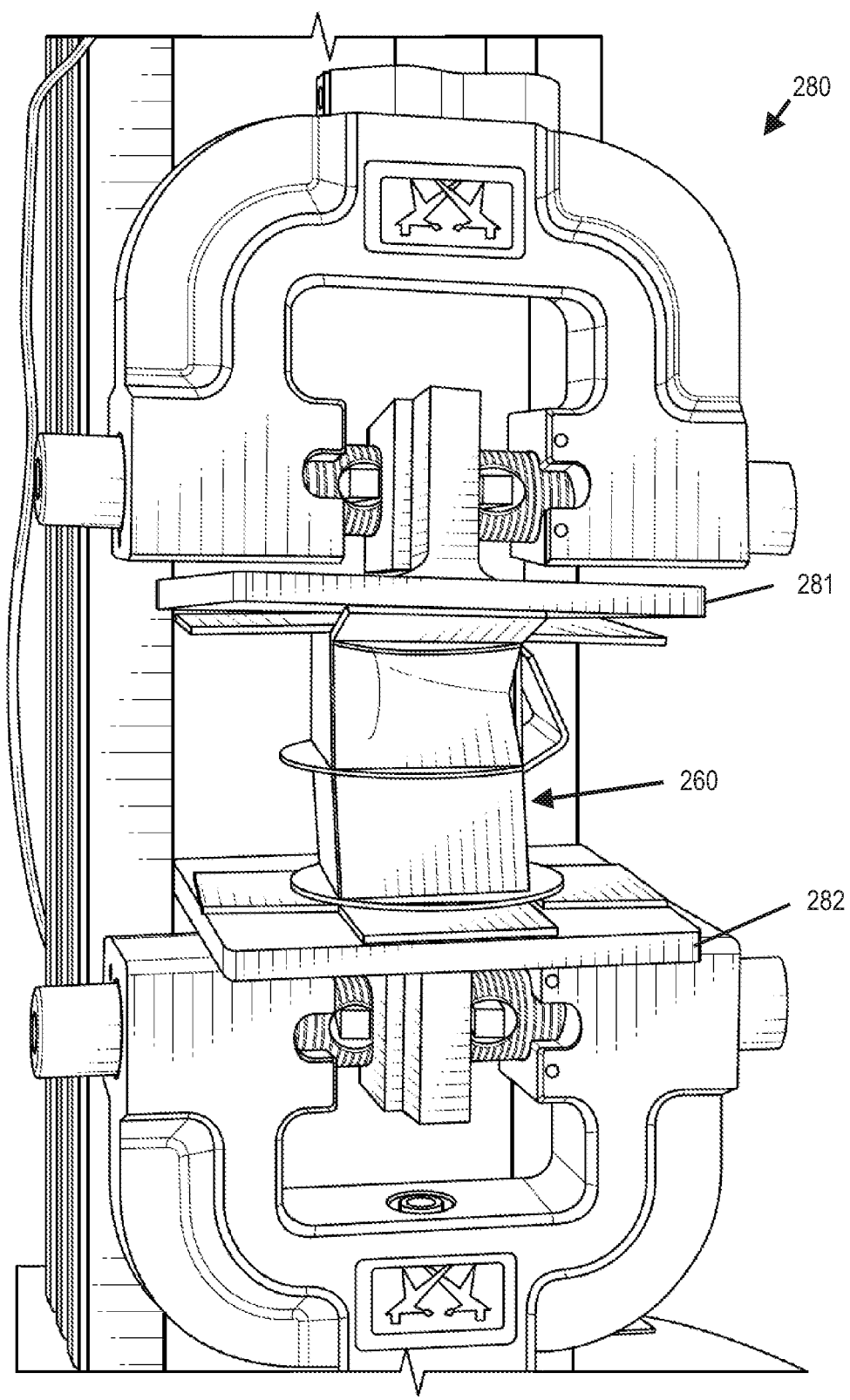
FIG. 9 is a perspective view image of the internal frame of FIG. 8 arranged in a compressive testing machine and being subjected to compression testing.

FIG. 9 is a perspective view image of the internal frame 260 of FIG. 8 arranged between first and second platens 281, 282 of a compressive testing machine 280 and being subjected to compression testing.

Figure 10:
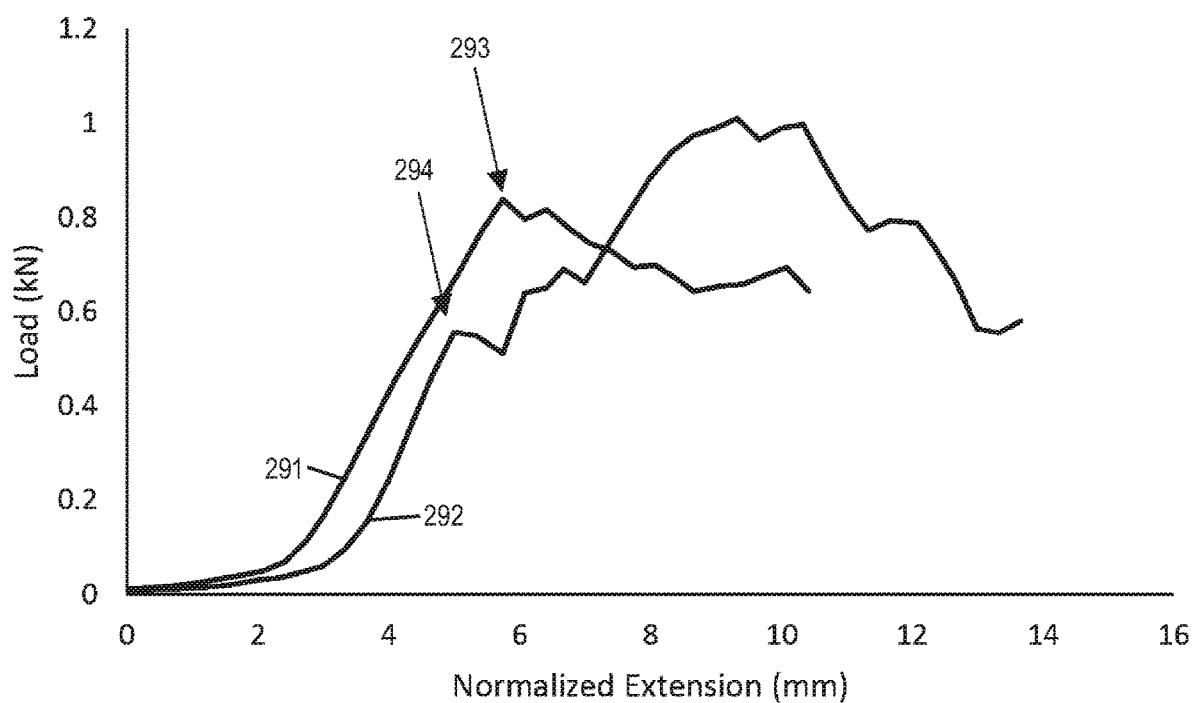
FIG. 10 is a plot of load (kN) versus normalized extension (mm) for the prosthetic frame samples of FIGS. 7 and 8 when subjected to compression testing.

FIG. 10 is a plot of load (kN) versus normalized extension (mm) for the prosthetic frame samples of FIGS. 7 and 8 when subjected to compression testing (with curve 291 corresponding to the frame design of FIG. 7, and curve 292 corresponding to the frame design of FIG. 8). Samples mechanically failed towards the ends of the samples instead of the middle FIG. 10 shows the compression curves 291, 292 of the data tended to follow one of two distinct shapes: a sharp incline, sharp peak (indicated by arrows 293, 294), and a slower decline; or a steep incline followed by a slower incline with multiple rounder peaks. This means that the design tended to follow only two modes of failure under compression in both location and in load bearing.

Figure 11:
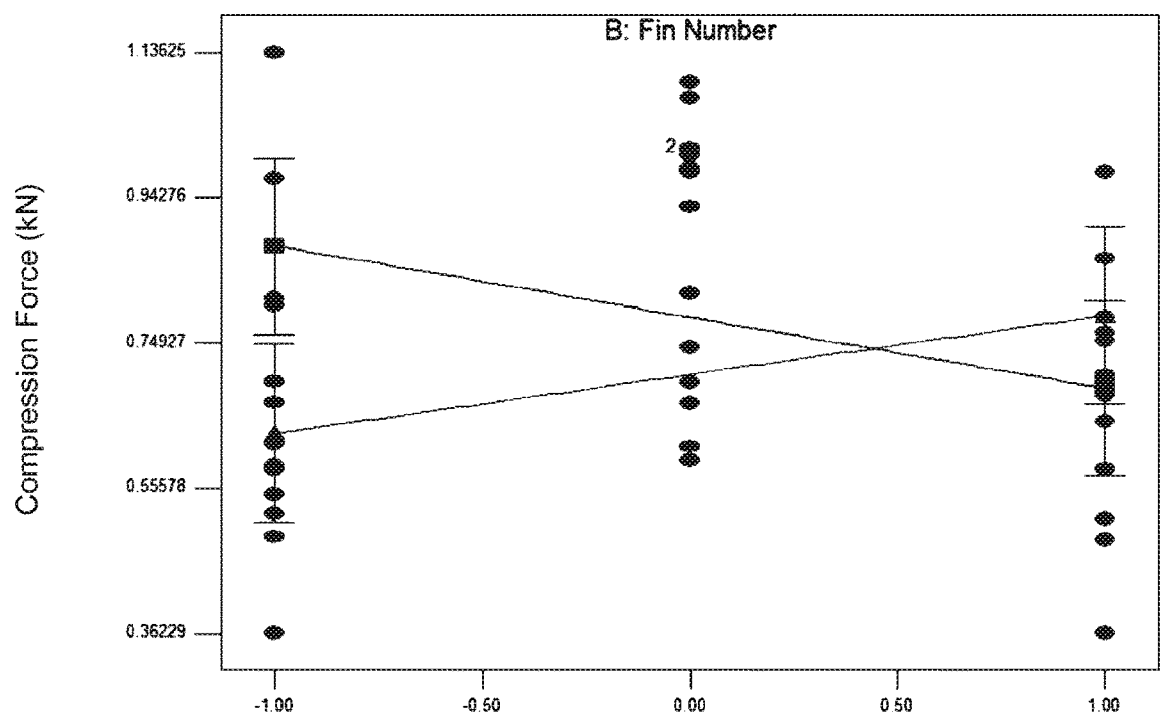
FIG. 11 is a first interaction graph of compression force (kN) versus hole radius (x axis: −1.00 equals 0 cm radius, and 1.00 equal 1.9 cm radius) and fin number (i.e., transverse member number).

The data was processed in DX6 in two stages. First with only the no hole, 1.1 cm radius hole, and 1.9 cm radius hole sample, as shown in FIG. 11. FIG. 11 is a first interaction graph of compression force (kN) versus hole radius (x axis: −1.00 equals 0 cm radius, and 1.00 equal 1.9 cm radius) and fin number (i.e., transverse member number). The black line denotes the three transverse member design, and the red line denotes the eleven transverse member design. Due to the larger error bars and the crossed lines for the find designs, T-tests were run comparing the four end points of the lines: eleven fin—no hole and three fin—1.9 cm radius hole versus eleven fin—1.9 cm radius hole and three fin—no hole. The test showed there was no significant difference in mean compression force between the two groups, meaning that adding a medial hole did not significantly alter the mechanical strength of the design.

Figure 12:
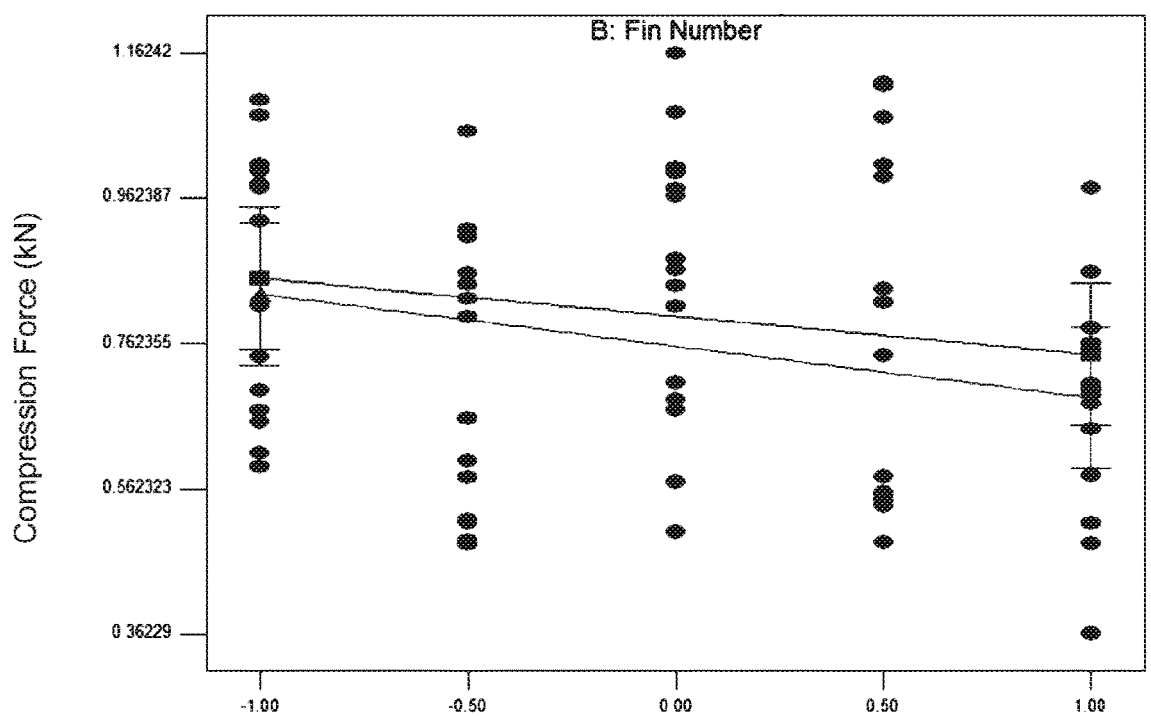
FIG. 12 is a second interaction graph of compression force (kN) versus hole radius (x axis: −1.00 equals 0 cm radius, and 1.00 equal 1.9 cm radius) and fin number (i.e., transverse member number).

DX6 was then run with all the sample data, except for the no-hole designs, as shown in FIG. 12. FIG. 12 is a second interaction graph of compression force (kN) versus hole radius (x axis: −1.00 equals 0 cm radius, and 1.00 equal 1.9 cm radius) and fin number (i.e., transverse member number). Though the lines in FIG. 12 are not crossed, the ends are much closer to each other, and large error bars are still present. T-testing again revealed there is no significant difference in the designs. This means that the sparsest design (three fin—1.9 cm radius hole) is just as compressively strong as the densest design (eleven fin—no hole) and can hold approximately 137 pounds. When this design is translated to stronger regulated materials, it can be expected to be even stronger. In fact, there is a possibility that the design will need to be even sparser to ensure a lack of excessive strength that would cause occurrence of the same problems as current rigid pylon-based prosthetic designs.

FIG. 13 is a table identifying average weight and interstitial volume values for internal frames of prosthetic devices according to four different designs. A first design included four transverse members ("fins") and no hole. A second design included four fins with a 1.9 cm radius hole. A third design included twelve fins and no hole. A fourth design included twelve fins with a 1.9 cm radius hole.

FIG. 14 is a table identifying percentage differences in weight and in interstitial volume for the latter three internal frame designs of FIG. 13 in comparison to one another and in comparison to the first internal frame design of FIG. 13. Calculated percentage differences between each of the extreme variables are provided. The sparsest design was 65.1% lighter and 10.4% more spacious than the densest design.

Figure 15A:
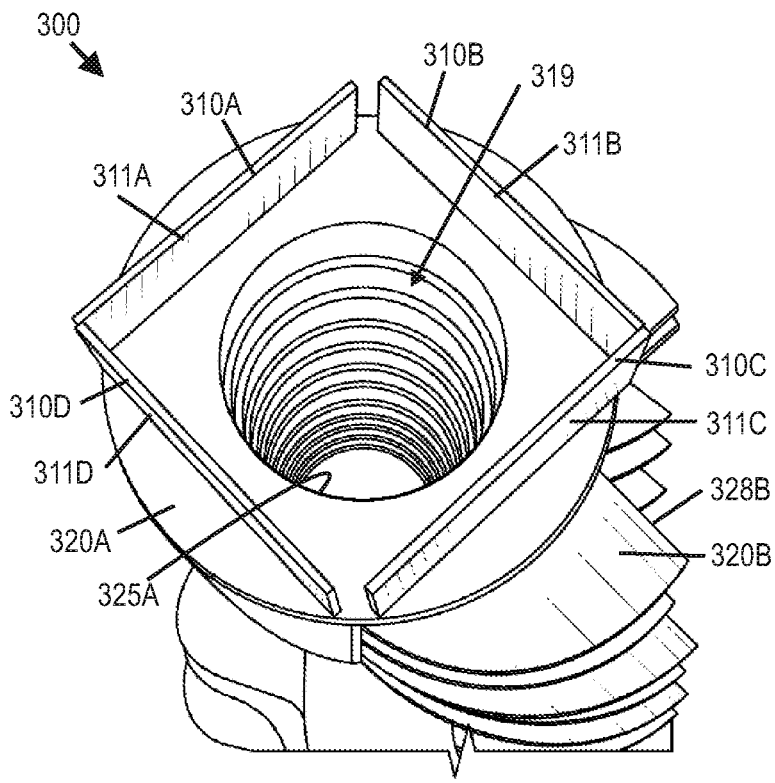
FIG. 15A is a lower perspective view illustration of an internal frame of a prosthetic device according to one embodiment, in which each transverse member defines a medial opening, and various transverse members having different sizes and shapes.
Figure 15B:
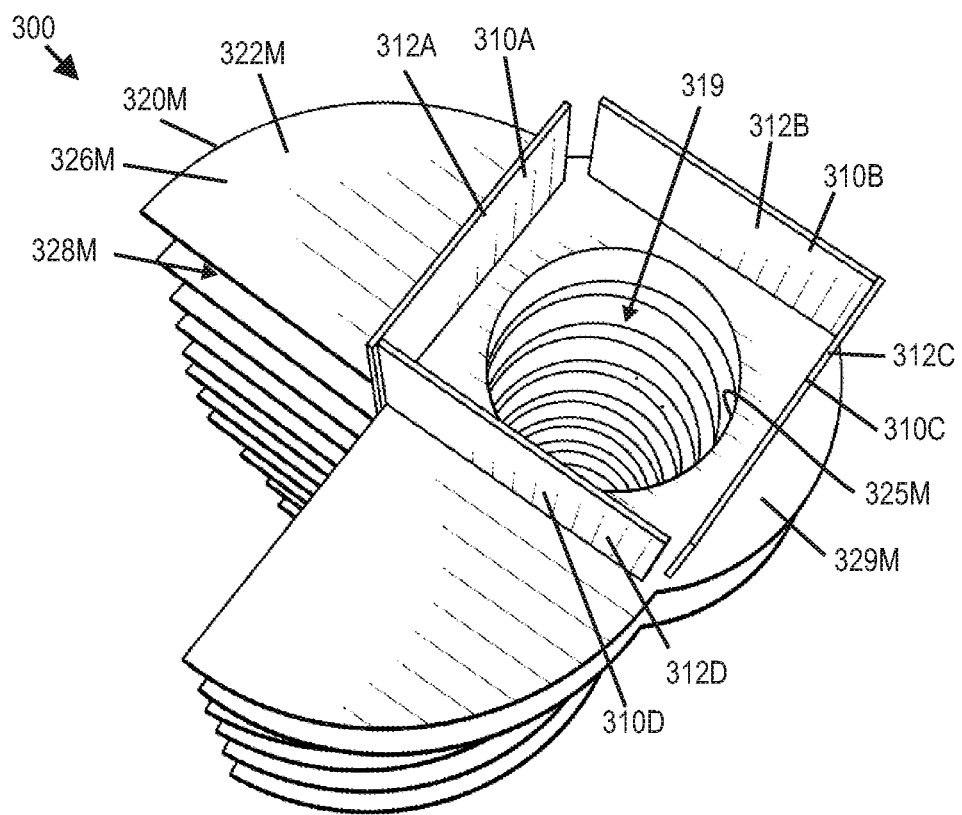
FIG. 15B is an upper perspective view photograph of the internal frame of FIG. 15A.

FIGS. 15A and 15B provide lower and upper perspective view illustrations, respectively, of an internal frame 300 of a prosthetic device according to one embodiment, including four longitudinal members 310A-310D (having lower ends 311A-311D and upper ends 312A-312D) and multiple transverse members 320A-320M of varying sizes and shapes.

Each transverse member 320A-320M defines a medial opening 325A-325M that in combination form a longitudinal passage 319 through the transverse members 320A-320M. The lowermost transverse member 320A is round in shape, whereas the uppermost transverse member 320M has a body 322M that includes a rounded portion 329M with two extension portions 326M of a partially rounded triangular shape and a generally triangular gap 328M between the two extension portions 326M. Other transverse members between the uppermost transverse member 320M and the lowermost transverse members 320A have sizes and shapes that generally transition between the sizes and shapes of the uppermost and lowermost transverse members 320M, 320A. The longitudinal passage 319 and the gap (e.g., gap 328M) in each transverse member 320A-320M may be used to contain and/or permit passage of one or more items such as actuators, dampers, batteries, electronics, wiring, and the like.

Figure 15C:
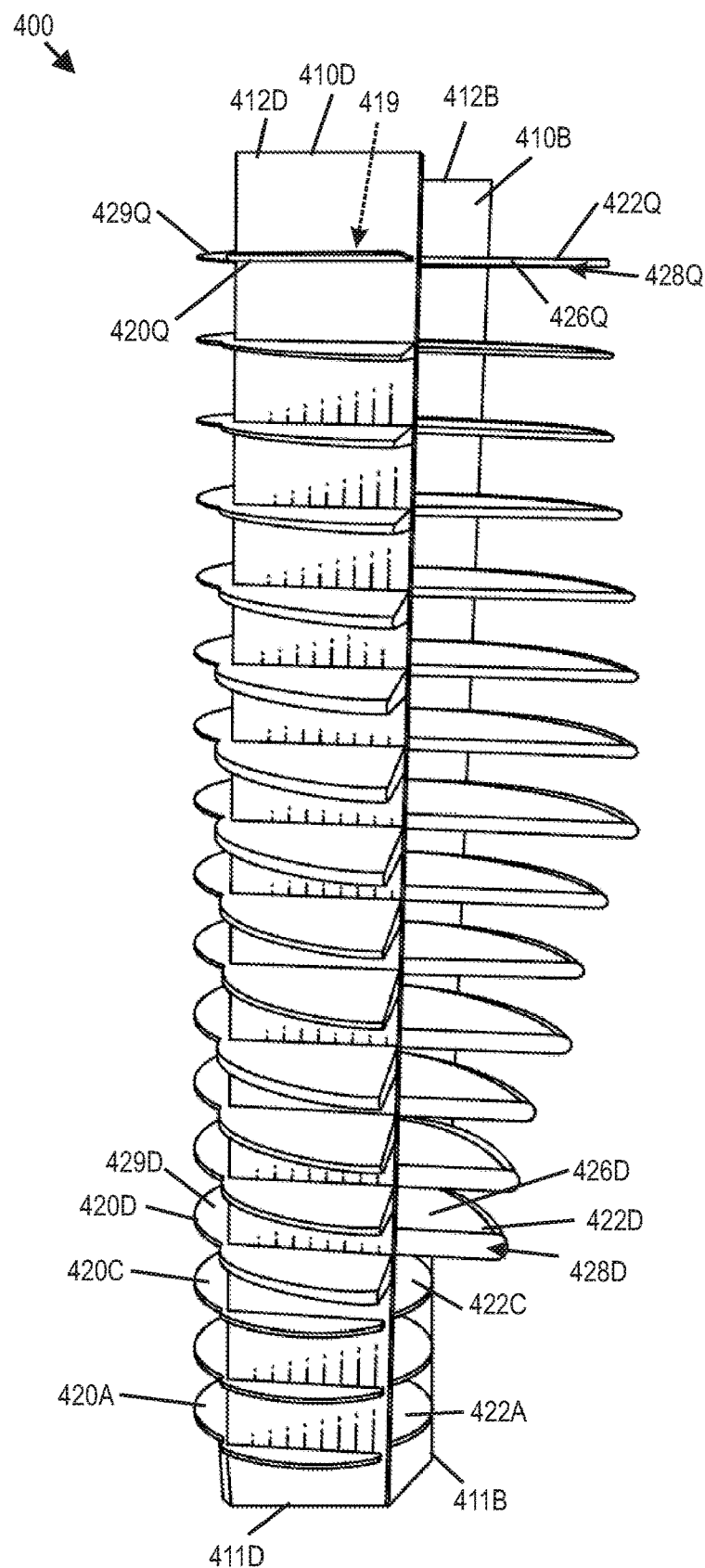
FIG. 15C is a side perspective view illustration of an internal frame 400 having a design similar to the frame design of FIGS. 15A and 15B.

FIG. 15C is a side perspective view illustration of an internal frame 400 having a design similar to the frame design of FIGS. 15A-15B. The internal frame 400 includes four longitudinal members 410A-410D (having lower ends 411A-411M and upper ends 412A-412M) and multiple transverse members 420A-420Q of varying sizes and shapes. Each transverse member 420A-420Q defines a medial opening (not shown) that in combination form a longitudinal passage 419 through the transverse members 420A-420Q. The lowermost three transverse members 420A-420C are round in shape, whereas the uppermost fourteen transverse members 420D-420Q each have a body 422D-422Q that includes a rounded portion 429D-429Q with two extension portions 426D-426Q of a partially rounded triangular shape and a generally rounded triangular gap 428D-428M between the two extension portions 426D-426Q. Other transverse members between the fourth and fourteenth transverse members 420D, 420Q have sizes and shapes that generally transition between the sizes and shapes of the fourth and fourteenth transverse members 420D, 420Q.

In one implementation, the internal frame 400 may have a height of about 37 cm. Below the knee amputations can occur anywhere along the lower leg, so the size of the internal frame can easily be adjusted or cropped to whatever length is needed for an individual recipient.

In certain embodiments, altering the design to mimic the shape of a human calf may not be structurally necessary, but does create an aesthetically similar shape to that of an existing leg. Such shape also provides extra interstitial space for the device, which could be beneficial once a prosthetic frame as disclosed herein is integrated with an actuated ankle.

For a full-sized prototype, the 6 fin—1.7 cm radius hole design was used and scaled up. A length of the transverse member (or "comb") was merely extended, with the tooth size remaining constant. The 1.7 cm radius hole design was used because the 1.9 cm radius hole fin was prone to tearing during assembly. It is assumed this is a chipboard material issue more than a design issue since assembly can be difficult due to the friction of the pieces. There was a concern that the use of four transverse members (or fins) would not have enough friction at a larger scale, so a design employing six transverse members or fins was used.

Figure 15D:
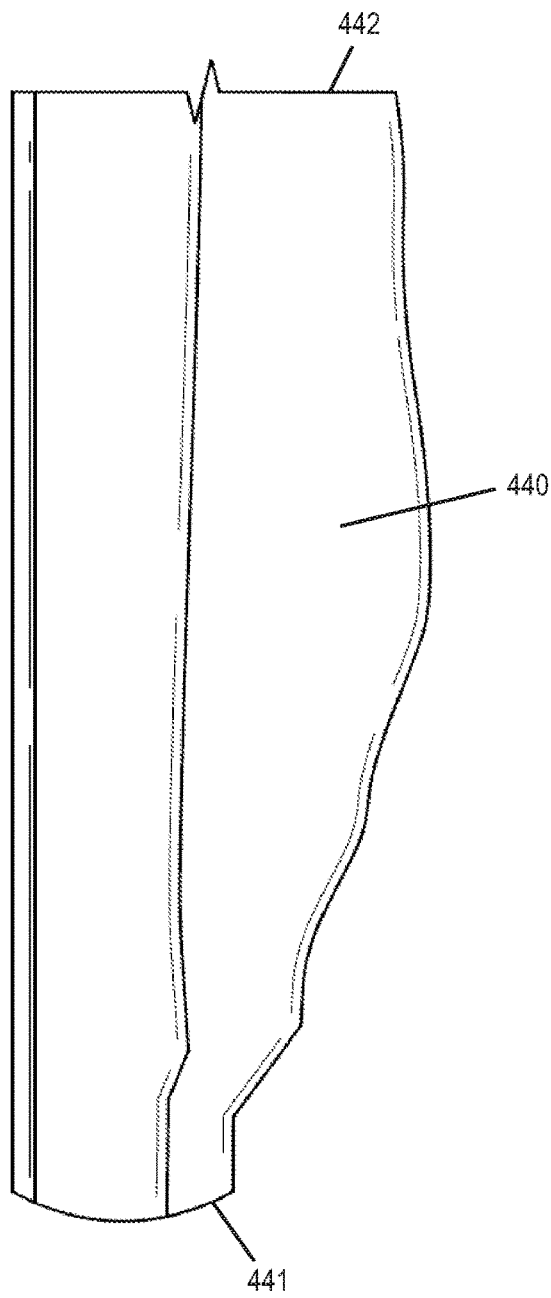
FIG. 15D is a side view illustration of an outer shaping member configured to extend over an outer periphery of the internal frame of FIG. 15C.
Figure 16:
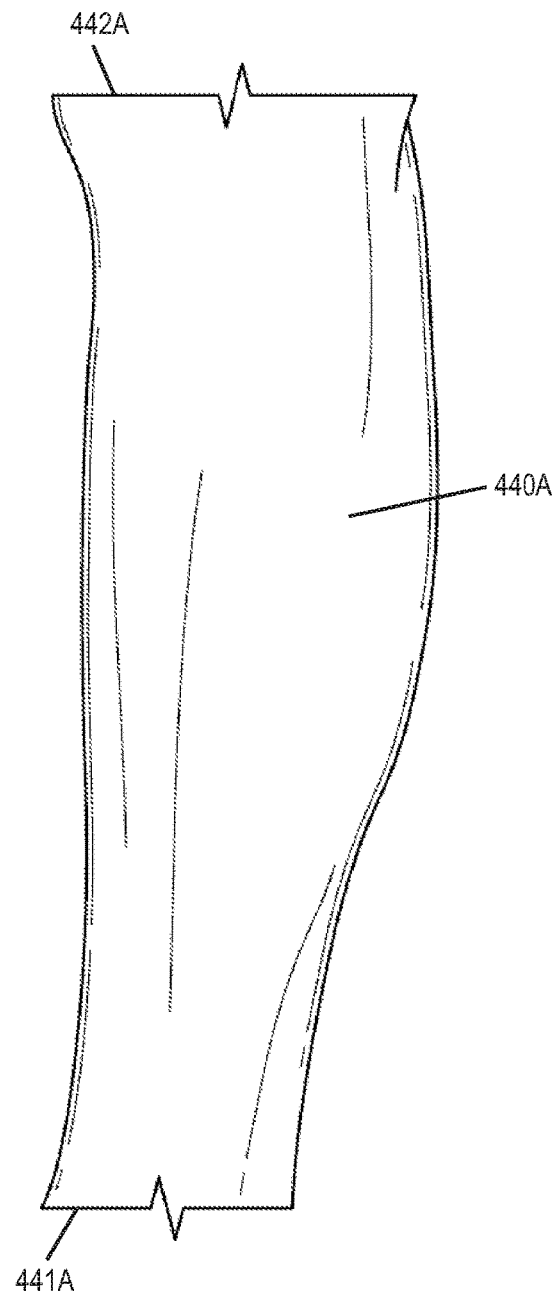
FIG. 16 is a photograph of a lower portion of a human leg that served as the basis for sizing and shaping the internal frame of FIG. 15.

FIG. 15D is a side view illustration of an outer shaping member 440 (having a lower portion 441 and an upper portion 442) configured to extend over an outer periphery of an internal frame 400 according to FIG. 15C. FIG. 16 illustrates a lower portion of a human leg 440A (having a lower portion 441A and an upper portion 442A) that was used as the basis for sizing and shaping the internal frame of FIG. 15C.

Figure 17:
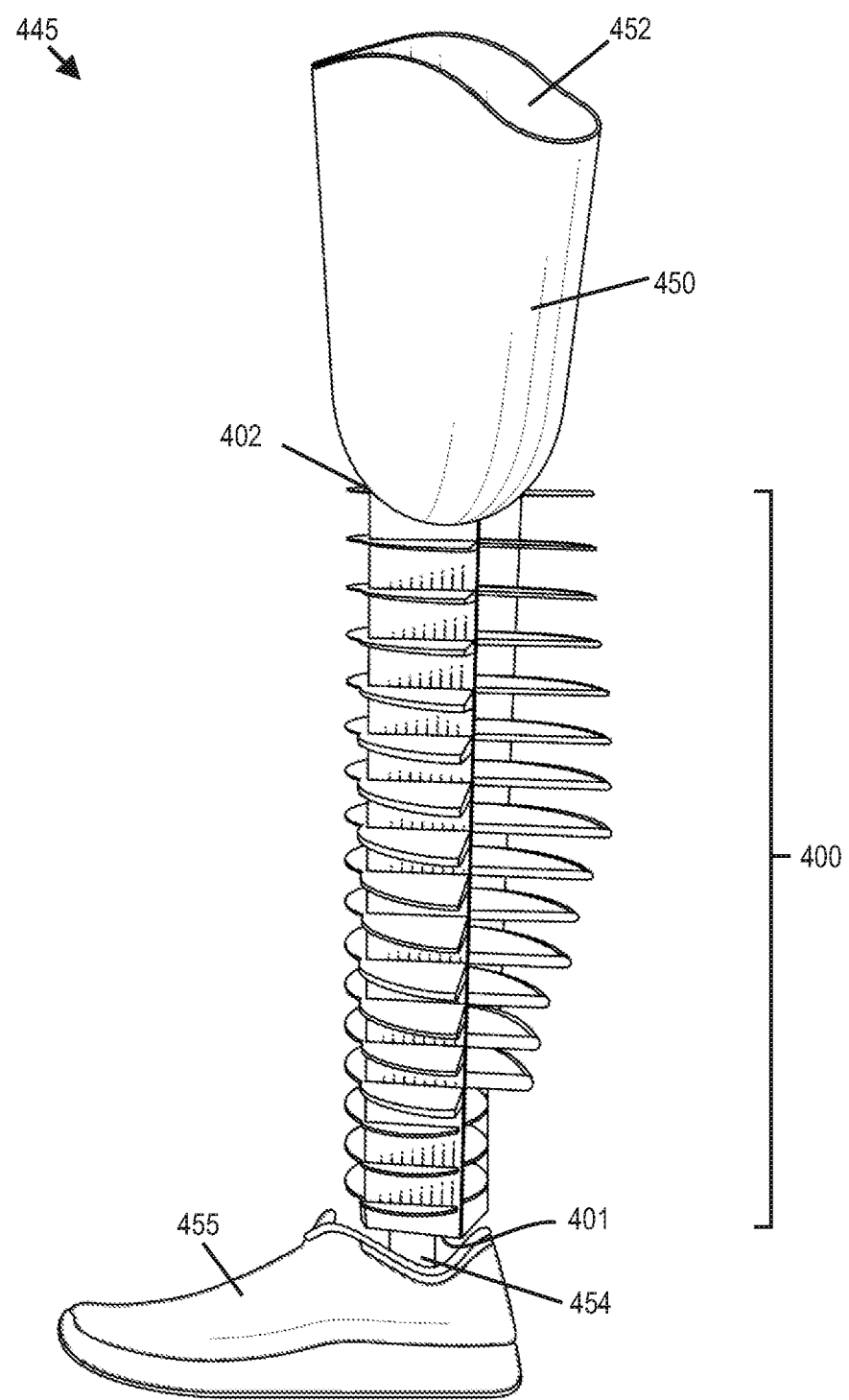
FIG. 17 is a perspective view illustration of portions of a prosthetic device including the internal frame of FIG. 15C, with a socket positioned at an upper end of the internal frame, and with a prosthetic foot positioned at a lower end of the internal frame.

FIG. 17 is a perspective view illustration of at least a portion of a prosthetic device 445 including the internal frame 400 of FIG. 15C, with a socket 450 positioned at an upper end 402 of the internal frame 400, and with a prosthetic foot 455 and shaft 454 positioned at a lower end 401 of the internal frame 400. The socket 450 includes an opening 452 configured to receive a leg portion of an amputee. Although only the internal frame 400 is shown between the socket 450 and the prosthetic foot 455, it is to be appreciated that one or more items such as actuators, dampers, batteries, etc. (not shown) may be arranged in or on the internal frame 400, and that a covering member (not shown) may be arranged over the internal frame 400.

Figure 18:
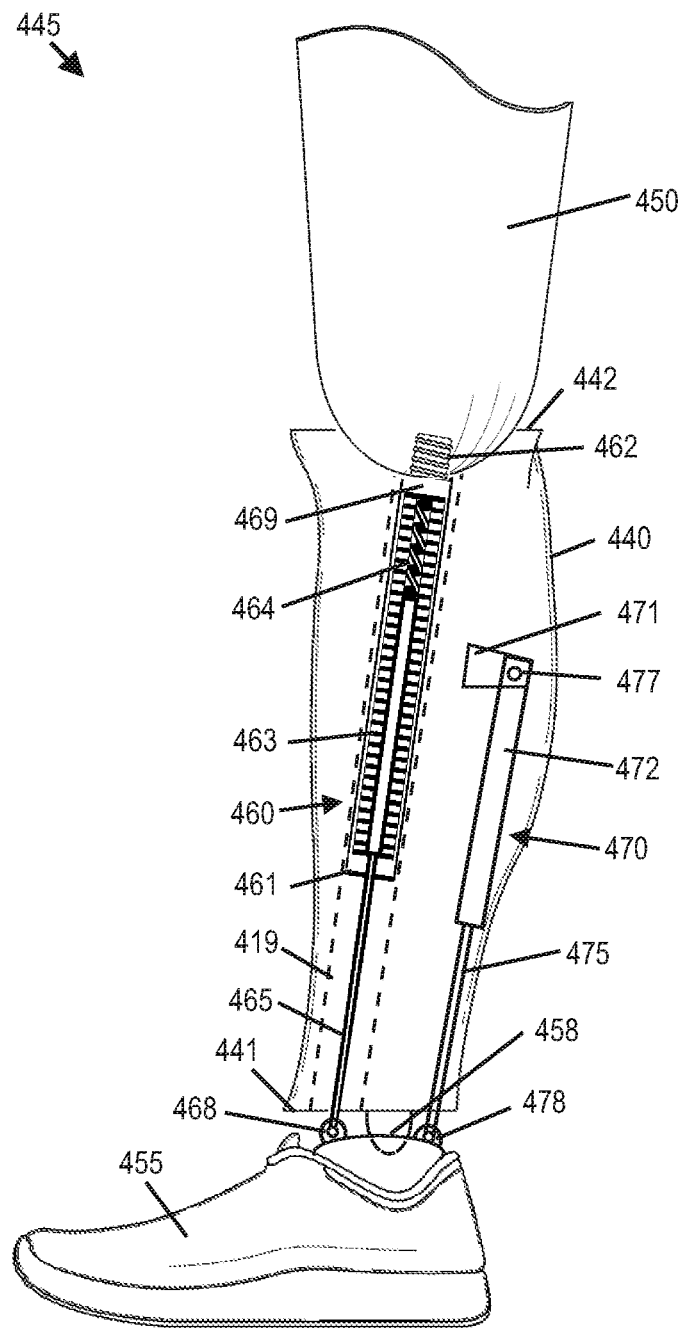
FIG. 18 is a elevational view illustration of further portions of the prosthetic device of FIG. 17, including actuator and damper elements configured to be received by the internal frame between the socket and prosthetic foot.

FIG. 18 is a elevational view illustration of portions of the prosthetic device 445 of FIG. 17, including a covering member 440, an actuator 460 configured to be received within the longitudinal passage 419 of the internal frame (not shown), and a damper 470 configured to be received in the triangular gaps of transverse members (not shown). Further illustrated are the socket 450 and the prosthetic foot 455 arranged at upper and lower ends 442, 441, respectively, of the internal frame (i.e., frame 400 shown in FIG. 17) of the prosthetic device 445. A threaded shaft 462 for mating within the socket 450 is provided at an upper portion of the covering member 440, optionally coupled with the actuator 460. The actuator 460 may be a magnetically actuated solenoid-type device with magnetic coils 463, a spring 464, and a moveable actuator shaft 465, and a body arranged between opposing ends 461, 469, with the moveable actuator shaft 465 being mounted to a forward pivotal linkage 468 associated with the prosthetic foot 455. In certain embodiments, the actuator 460 is configured to be bidirectionally actuated. The damper 470 may be secured with a mounting bracket 471 proximate to an upper pivotal linkage 477, and may include a damper body 472 and an associated moveable damper shaft 475 that is coupled to a rearward pivotal linkage 478 associated with the prosthetic foot 455. In certain embodiments, the damper 470 may be supplemented or supplanted with a second actuator (e.g., a bidirectional magnetic solenoid-type actuator). The prosthetic foot 455 may further include a central pivotal linkage 458 for coupling to an internal frame (i.e., frame 400 shown in FIG. 17) of the prosthetic device 445.

FIG. 19 is a top plan view illustration of a substantially planar transverse member 520 arranged to form a lower portion of an internal frame of prosthetic device according to one embodiment. In certain embodiments, the transverse member 520 may be used in an ankle region (e.g., as fifteenth to seventeenth transverse members in a transtibial prosthetic device). The transverse member 520 includes a generally round body 522 defining a medial opening 525 and defining four peripheral slots 528, arranged as two pairs of slots 528 each in a chevron configuration. The medial opening 525 is bounded by an edge 531 and is arranged between the pairs of slots 528. Each pair of slots 528 has a single slot opening 529 arranged along an outer edge 527 of the body 522.

FIG. 20 is a top plan view illustration of a substantially planar transverse member 540 arranged to form an upper lower portion of an internal frame of prosthetic device according to one embodiment. In certain embodiments, the transverse member 540 may be used in a calf region (e.g., as the seventh transverse member in a transtibial prosthetic device). The transverse member 540 embodies a shape resembling a merger between two circular shapes, with the lower circular shape having a larger diameter, and with a medial opening 545 (e.g., being round in shape) arranged at an intersection between the two circular shapes. The transverse member 540 has a body 542 that includes a rounded portion 549 and includes two extension portions 546 of a partially rounded triangular shape, with a generally triangular gap 548 arranged between the two extension portions 546. Two pairs of slots 558 are provided, with each pair of slots 558 being arranged in a chevron shape, and each pair of slots 558 having a single slot opening 559 arranged along an outer edge 557 of the body.

Multiple transverse members 520, 540 according to FIGS. 19 and 20 may be used in combination with multiple longitudinal members (e.g., longitudinal member 220 shown in FIG. 3) to form an internal frame of a prosthetic device.

An algorithm was developed for converting a basic cylindrical design into a leg shape. A leg circumference was measured in 2 cm increments. An original transverse member design was scaled to a smallest circumference (typically just above the ankle), with this size being a "base size". A larger (i.e., lower as illustrated) half of the transverse member is scaled to the changed circumference of the lower half. FIG. 21 is a table identifying seven dimensional values for each of two transverse members (or fins) of a prosthetic device incorporating the transverse members of FIGS. 19 and 20 according to the foregoing algorithm. "Fin 0" corresponds to the transverse member of FIG. 19, whereas "Fin 14" corresponds to the transverse member of FIG. 20. For dimensions a, b, c, d, f, and g, values in the second column are 1.3 times the value in the first column, whereas for dimension e, the value in the second column is 1.243 times the value in the first column.

Technical benefits of frames disclosed herein include: high compressive strength, comparable torsional strength, increased internal free space volume provided by medial openings extending between transverse members; increased free space provided by peripheral openings defined in transverse members; ease of scalability and/or tailoring to individual patients; and rapid and economical production. Moreover, moving from a conventional endoskeletal (e.g., titanium post) prosthetic frame design to designs disclosed herein may allow for improved gait mechanics, shock absorption, and aesthetics. Improved shock absorption and gait mechanics may prevent further injuries in upper leg, hips, spine, and neck of prosthetic limb users. Sparser designs leave significantly more room to package electronics, motors, actuators, etc. into a prosthetic device without disrupting aesthetics of the prosthetic device shape.

Those skilled in the art will recognize improvements and modifications to the preferred embodiments of the present disclosure. All such improvements and modifications are considered within the scope of the concepts disclosed herein and the claims that follow. Any of the various features and elements as disclosed herein may be combined with one or more other disclosed features and elements unless indicated to the contrary herein.

What is claimed is:

1. A prosthetic device sized and shaped to correspond to at least a portion of a limb of a human user, the prosthetic device comprising:
an internal frame that comprises:
a plurality of longitudinal members, wherein each longitudinal member of the plurality of longitudinal members is substantially planar and comprises a plurality of first peripheral slots defined through an entire thickness of the respective longitudinal member; and
a plurality of transverse members, wherein each transverse member of the plurality of transverse members is substantially planar and comprises a plurality of second peripheral slots defined through an entire thickness of the respective transverse member;
wherein each first peripheral slot of the plurality of first peripheral slots is arranged to mate with a different second peripheral slot of the plurality of second peripheral slots, to join the plurality of longitudinal members with the plurality of transverse members;
wherein each transverse member defines a medially arranged opening, and the medially arranged opening of each transverse member is substantially registered with the medially arranged opening of at least one adjacent transverse member; and
wherein at least some transverse members of the plurality of transverse members differ from other transverse members of the plurality of transverse members in one or more of shape, length, or width.

2. The prosthetic device of claim 1, wherein the plurality of longitudinal members is devoid of any longitudinal members that are radially arranged relative to a central axis extending through the plurality of transverse members.

3. The prosthetic device of claim 2, wherein longitudinal members of the plurality of longitudinal members are tangentially arranged relative to an imaginary circle concentrically arranged with the central axis, wherein the imaginary circle comprises a diameter smaller than a lateral extent of each transverse member of the plurality of transverse members.

4. The prosthetic device of claim 1, further comprising at least one of an actuator or a control element extending through medially arranged openings of multiple transverse members of the plurality of transverse members.

5. The prosthetic device of claim 1, wherein two or more transverse members of the plurality of transverse members each define a peripheral recess, wherein for each transverse member of the two or more transverse members, at least two peripheral slots of the plurality of second peripheral slots extend from the peripheral recess into an interior of the transverse member without intersecting the medially arranged opening.

6. The prosthetic device of claim 5, wherein the peripheral recess of each transverse member of the two or more transverse members is registered with the peripheral recess of each other transverse member of the two or more transverse members.

7. The prosthetic device of claim 1, wherein two or more transverse members of the plurality of transverse members each define a peripheral recess, wherein the peripheral recess of each transverse member of the two or more transverse members is registered with the peripheral recess of each other transverse member of the two or more transverse members.

8. The prosthetic device of claim 7, further comprising at least one of an actuator, an energy storage element, a sensor, or a control element arranged in the peripherally arranged recesses of the two or more transverse members.

9. The prosthetic device of claim 1, further comprising an outer shaping member arranged to cover and compressively engage at least a portion of the internal frame.

10. The prosthetic device of claim 1, wherein at least two transverse members of the plurality of transverse members are arranged substantially perpendicular to the plurality of longitudinal members.

11. The prosthetic device of claim 1, wherein the plurality of transverse members is bonded to the plurality of longitudinal members.

12. The prosthetic device of claim 1, wherein at least some members of at least one of (i) the plurality of longitudinal members or (ii) the plurality of transverse members comprises polymeric materials.

13. The prosthetic device of claim 1, wherein at least some members of at least one of (i) the plurality of longitudinal members or (ii) the plurality of transverse members comprises paperboard materials, wood fiber-based materials, or laminated composite materials.

14. The prosthetic device of claim 1, wherein at least some members of at least one of (i) the plurality of longitudinal members or (ii) the plurality of transverse members comprises metals or metallic materials.

15. The prosthetic device of claim 1, wherein the plurality of longitudinal members consists of four longitudinal members.

16. The prosthetic device of claim 1, further comprising a socket positioned at an upper end of the internal frame, wherein the socket is configured to receive a residual limb of the human user.

17. A method for fabricating a prosthetic device according to claim 1, the method comprising mating each first peripheral slot of the plurality of first peripheral slots with a different second peripheral slot of the plurality of second peripheral slots to join the plurality of substantially planar longitudinal members with the plurality of substantially planar transverse members to form the internal frame of the prosthetic device.

18. The method of claim 17, further comprising bonding at least some transverse members of the plurality of substantially planar transverse members to the plurality of substantially planar longitudinal members.

19. The method of claim 17, further comprising providing an outer shaping member to cover at least a portion of the internal frame.

20. The method of claim 17, further comprising measuring one or more dimensions of a prosthetic recipient, and fabricating (i) the plurality of substantially planar longitudinal members and/or (ii) the plurality of substantially planar transverse members responsive to said measuring.

21. The method of claim 17, further comprising fabricating at least some members of (i) the plurality of substantially planar longitudinal members and/or (ii) the plurality of substantially planar transverse members by at least one step selected from thermoforming, molding, stamping, or casting.

22. The method of claim 17, further comprising fabricating at least some members of (i) the plurality of substantially planar longitudinal members and/or (ii) the plurality of substantially planar transverse members by at least one step selected from milling, blade cutting, laser cutting, or liquid jet cutting.

23. The method of claim 17, further comprising fabricating at least some members of (i) the plurality of substantially planar longitudinal members and/or (ii) the plurality of substantially planar transverse members by at least one step selected from three-dimensional printing or multi-layer additive material deposition.

* * * * *